United States Patent [19]

Kitano et al.

[11] Patent Number: 4,853,486

[45] Date of Patent: Aug. 1, 1989

[54] METHOD FOR PRODUCTION OF DITHIODIALDEHYDE

[75] Inventors: Masao Kitano, Yokohama; Tsunemasa Ueno; Kouichi Kojima, both of Kawasaki; Yutaka Morimoto, Yokohama, all of Japan

[73] Assignee: Nippon Shokubai Kagaku Kogyo Co., Ltd., Osaka, Japan

[21] Appl. No.: 204,039

[22] Filed: Jun. 7, 1988

[51] Int. Cl.$^4$ .......................................... C07C 148/00
[52] U.S. Cl. .................................................. 568/22
[58] Field of Search ................................. 568/22, 41

[56] References Cited

U.S. PATENT DOCUMENTS 2,580,695 1/1952 Niederhauser ..................... 568/22

Primary Examiner—Mary E. Ceperley
Attorney, Agent, or Firm—Omri M. Behr

[57] ABSTRACT

In a method for the production of a dithiodialdehyde represented by the formula II:

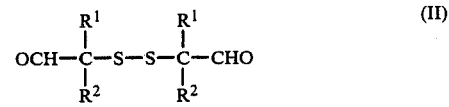

wherein $R^1$ and $R^2$ are independently alkyl group of 1 to 8 carbon atoms, by condensation of an active hydrogen-containing aldehyde represented by the formula I:

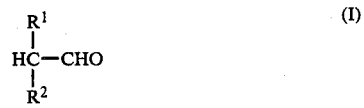

wherein $R^1$ and $R^2$ have the same meanings as defined above, with sulfur monochloride, the improvement which comprises simultaneously supplying said active hydrogen-containing aldehyde and sulfur monochloride to an inactive solvent, or adding said active hydrogen-containing aldehyde to a mixture of said inactive solvent with the sulfur monochloride.

12 Claims, No Drawings

METHOD FOR PRODUCTION OF DITHIODIALDEHYDE

BACKGROUND OF THE INVENTION

1. Field of the Invention

This invention relates to a method for the production of dithiodialdehydes.

2. Description of the Prior Art

Dithiodialdehydes are useful by themselves as a cross-linking agent and are useful as intermediates for medicines, agricultural pesticides, photographic chemicals, resin improving agents, etc. The mercaptoaldehydes represented by the general formula III:

wherein $R^1$ and $R^2$ are independently alkyl group of 1 to 8 carbon atoms, are easily obtained by the reduction of dithiodialdehydes. The tertiary thiol group-containing amines represented by the general formula IV:

wherein $R^1$ and $R^2$ have the same meanings as defined above and R is hydrogen or alkyl group of 1 to 24 carbon atoms are easily obtained by causing various primary amines to react on dithiodialdehydes thereby producing corresponding Schiff bases and subsequently reducing the Schiff bases. The compounds represented by these formulas III and IV are also useful as intermediates for medicines, agricultural pesticides, photographic chemicals, resin improving agents, etc.

The method for producing dithiodialdehydes represented by the general formula II:

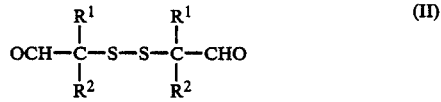

wherein $R^1$ and $R^2$ are independently alkyl group of 1 to 8 carbon atoms, by condensing active hydrogen-containing aldehydes represented by the formula I:

wherein $R^1$ and $R^2$ have the same meanings as defined above, with sulfur monochloride has been disclosed in U.S. Pat. No. 2,580,695, for example. This condensation is carried out by dissolving in an inactive solvent an active hydrogen-containing aldehyde, one of the two raw materials for the reaction, and then adding sulfur monochloride, the other raw material, to the resultant solution.

By experimentally repeating this method, we have learnt that this method gives the product in a low yield of the order of 50 to 60%. On analysis by gas chromatography, the product of this reaction is found to contain various impurities which are thought to be decomposition products of aldehyde. An increase in the time spent for the addition of sulfur monochloride has been found to lower the yield of the reaction and the purity of the product. Since this reaction is highly exothermal, the control of the reaction temperature necessitates exact control of the speed of addition of sulfur monochloride. A method of such a nature cannot be effectively carried out on a commercial scale to obtain the product with highly stable yield and purity.

An object of this invention, therefore, is to provide an improved method for the production of a dithiodialdehyde.

Another object of this invention is to provide an economically advantageous method capable of producing a dithiodialdehyde in a high yield with a high purity without entailing the aforementioned drawbacks suffered by the conventional method.

SUMMARY OF THE INVENTION

The objects described above are accomplished in the production of a dithiodialdehyde represented by the formula II:

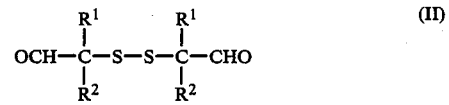

wherein $R^1$ and $R^2$ are independently alkyl group of 1 to 8 carbon atoms, by the condensation of an active hydrogen-containing aldehydes represented by the formula I:

wherein $R^1$ and $R^2$ have the same meanings as defined above, with sulfur monochloride, by providing an improved method which comprises causing the active hydrogen-containing aldehyde and sulfur monochloride to be simultaneously supplied into an inactive solvent and allowed to react therein.

The objects are also accomplished, in the production of a dithiodialdehyde represented by the formula II by the condensation of an active hydrogen-containing aldehyde represented by the formula I with sulfur monochloride, by providing an improved method which comprises adding the active hydrogen-containing aldehyde into a mixture of an inactive solvent with sulfur monochloride and allowing the active hydrogen-containing aldehyde to react with sulfur monochloride in the mixture.

Our elaborate study on the method disclosed in the U.S. Pat. No. 2,580,695 has revealed that the yield and the purity of the produced dithiodialdehyde have been lowered by the hydrogen chloride gas by-produced during the reaction. To be more specific, the hydrogen chloride gas catalytically acts on the active hydrogen-containing aldehyde and accelerates the decomposition and polymerization of the aldehyde and consequently lower the yield and the purity of the produced dithiodialdehyde. We have continued a study with a view to solving the problem and, as the result, perfected the present invention.

DESCRIPTION OF PREFERRED EMBODIMENTS

The method of this invention is effected firstly by supplying simultaneously an active hydrogen-containing aldehyde and sulfur monochloride into an inactive solvent with the molar ratio of the active hydrogen-containing aldehyde to the sulfur monochloride so fixed that the reaction will proceed while the sulfur monochloride is present in not less than an equivalent weight, preferably always in an excess of equivalent weight, relative to the active hydrogen-containing aldehyde.

Otherwise, the method of this invention is effected secondly by adding the active hydrogen-containing aldehyde into a mixture of the inactive solvent with the sulfur monochloride and allowing the active hydrogen-containing aldehyde to react with the sulfur monochloride in the mixture. In this reaction, the molar ratio of the active hydrogen-containing aldehyde to the sulfur monochloride is so fixed that the reaction will proceed while the sulfur monochloride is present always in not less than a equivalent weight relative to the active hydrogen-containing aldehyde.

The significance of the constant presence of the sulfur monochloride in not less than an equivalent weight in the reaction mixture relative to the active hydrogen-containing aldehyde throughout the entire period of the reaction comprises substantially eliminating persistence of the active hydrogen-containing aldehyde thereby precluding creation of contact between the by-produced hydrogen chloride gas and the active hydrogen-containing aldehyde.

When the reaction is carried out by this method, the dithiodialdehyde can be produced in a high yield with high purity without reference to the time to be spent in the addition of raw materials.

The active hydrogen-containing aldehyde represented by the general formula I is desired to be an alkyl aldehyde having 1 to 8, preferably 1 to 4, carbon atoms independently in the substituents, $R^1$ and $R^2$. Typical examples of this alkyl aldehyde include isobutyl aldehyde, 2-methylbutyl aldehyde, 2-ethylbutyl aldehyde, 2-ethylhexyl aldehyde, 2-butylhexyl aldehyde, 2-butyldecyl aldehyde, and 2-octyldecyl aldehyde.

The reaction is carried out at a temperature in the range of 0° to 100° C. Since the reaction velocity increases and paradoxically the amount of by-products also increases in proportion as the reaction temperature rises, the reaction temperature is desirably in the range of 10° to 60° C. The reaction is carried out under normal pressure so that the by-produced hydrogen chloride gas is released into the ambience.

The reaction time is reckoned as lasting substantially until the reaction terminates. Generally, the period of 30 minutes which follows completion of the addition of the active hydrogen-containing aldehyde is sufficient for this purpose.

Isolation of the dithiodialdehyde, the target of this invention, from the reaction mixture can be carried out as follows. Water is thrown in the reaction mixture to induce hydrolysis of the sulfur monochloride remaining in a minute amount therein, absorption of the hydrogen chloride gas within the system, and subsequent separation of the reaction mixture into two layers. As the result, the dithiodialdehyde can be separated in the form dissolved in the organic layer. Thereafter, it can be obtained easily in a purified state by recovering the solvent from the organic layer and distilling the remaining organic layer.

The term "inactive solvent" is used in the sense that the solvent is substantially incapable of reacting with the raw materials and the product under the reaction conditions. The solvent to be used is desired to be incapable of dissolving the by-produced hydrogen chloride gas. Suitably, this solvent is an aromatic hydrocarbon solvent or a halogenated hydrocarbon solvent. Typical examples of the aromatic hydrocarbon solvent include benzene, toluene, xylene, chlorobenzene, and dichorobenzene. Typical examples of the halogenated hydrocarbon solvent include methylene chloride, trichloromethane, carbon tetrachloride, ethylene dichloride, and ethylene trichloride.

The molar ratio of the active hydrogen-containing aldehyde to the sulfur monochloride to be used in the reaction is desired to be such that the amount of the sulfur monochloride falls in the range of 1.0 to 1.2 equivalent weights, preferably 1.0 to 1.02 relative to the amount of the active hydrogen-containing aldehyde.

If the reaction proceeds while the active hydrogen-containing aldehyde is present in an excess amount, the yield and the purity are lowered by such secondary reactions as decompositoin and polymerization. If the sulfur monochloride is present in an excess amount, the excess is uneconomical because it is only used in the formation of hydrogen chloride gas and sulfur by decomposition. For above reason, the equivalent amount is the most preferable.

Now, the present invention will be described more specifically below with reference to working examples, which are illustrative, not limitative, of the present invention.

EXAMPLE 1

In a flask provided with a stirrer, a thermometer, a reflux condenser, and two dropping funnels were set. Separately a line adapted for causing absorption of by-produced hydrogen chloride gas by an aqueous alkali solution was attached to the upper part of the reflux condenser.

In the reaction flask thus prepared, 360 gr of methylene chloride as a solvent was placed and heated to 30° C. One of the dropping funnels was filled with 144 gr of isobutyl aldehyde and the other dropping funnel with 135 gr of sulfur monochloride and the dropping funnels are set in the reaction flask.

From the dropping funnels, isobutyl aldehyde and sulfur monochloride were introduced dropwise into the reaction flask over a period of about 60 minutes at a ratio such that the reaction would proceed always in the presence of sulfur monochloride in an excess of equivalent weight (roughly 0 to 10%). The reaction temperature was either 30° C. or the point at which the solvent was refluxed. The temperature during the course of the reflux was 38° C. The reaction mixture was left aging at 38° C. for 30 minutes following completion of the dropwise addition of isobutyl aldehyde. Then, 300 ml of water was added to the reaction mixture and left refluxing for 30 minutes to effect hydrolysis of sulfur monochloride still remaining in a very small amount in the mixture. The temperature of the reaction system at this point was 48° C. After terminating of the reflux, the reaction system was cooled to below 30° C. to induce separation of the reaction mixture into two layers. When the organic layer was separated and analyzed by gas chromatography, the yield of dithiodiisobutyl aldehyde based on isobutyl aldehyde was found to be 89%.

When the oil remaining after recovery of methylene chloride as solvent from the organic layer was analyzed by gas chromatography, it was found to contain the dithiodibutyl aldehyde in a purity of 92% of parity and also contain about 7% of by-produced trisulfide.

When the oil was further distilled under the conditions of 100° to 115° C. (1 mmHg), exceeding 97% was obtained in a yield of 85% based on isobutyl aldehyde as the raw materials.

EXAMPLE 2

The procedure of Example 1 was repeated, except that the time spent for the addition of isobutyl aldehyde and sulfur monochloride as raw materials was changed from 60 minutes to five hours. The yield of reaction was 90%. The purity of dithiodiisobutyl aldehyde in the oil remaining after recovery of the solvent was 92%, indicating that the difference in the time for addition brought about no discernible difference in yield and purity.

EXAMPLE 3

In a flask provided with a stirrer, a thermometer, a reflux condenser, and a dropping funnel were set and a line adapted to effect absorption of by-produced hydrogen chloride gas by an aqueous alkali solution was separately attached to the upper part of the reflux condenser.

Preferatory to the reaction, the flask was charged with 360 gr of methylene chloride and 135 gr of sulfur monochloride and heated to raise the temperature of the contents to 30° C. Through the dropping funnel, 144 gr of isobutyl aldehyde was introduced dropwise into the reaction flask over a period of about 60 minutes to induce reaction. The reaction temperature was 30° C. to the point at which the solvent was refluxed. The temperature was 38° C. during the course of the reflux. The reaction mixture was left aging at 38° C. for 30 minutes following termination of the dropwise introduction of isobutyl aldehyde. Then, after adding 300 ml of water, the reaction mixture were left under refluxing for 30 minutes to induce hydrolysis of sulfur monochloride still remaining in a very small amount therein. The temperature of the reaction system at this point was 48° C. After completion of the hydrolysis, the reaction mixture was cooled to below 30° C. to induce separation of the reaction mixture into two layers. When the organic layer was separated and then analyzed by gas chromatography, the yield of dithioisobutyl aldehyde relative to isobutyl aldehyde was found to be 90%.

When the oil remaining after recovery of methylene chloride as solvent from the organic layer was analyzed by gas chromatography, it was found to contain dithioisobutyl aldehyde in a purity of 92% and also contain about 7% of by-produced trisulfide.

When the oil was further distilled under the conditions of 100° to 115° C. (1 mmHg), the dithiodiisobutyl aldehyde of a purity of not less than 97% was obtained in a yield of 85% based on isobutyl aldehyde as the raw material.

EXAMPLE 4

The procedure of Example 3 was repeated, except that the time spent for the addition of isobutyl aldehyde as raw material was changed from 60 minutes to five hours. The yield of reaction in this case was 90%. In the oil remaining after recovery of the solvent, the purity of dithiodiisobutyl aldehyde was 92%, indicating that the difference in the time of addition brought about no discernible difference in yield or purity.

CONTROL 1

In a flask provided with a stirrer, a thermometer, a reflux condenser, and a dropping funnel were set and a hydrogen chloride gas absorption line was attached similarly to Example 1.

In the reaction flask thus prepared, 360 gr of methylene chloride as a solvent and 144 gr of isobutyl aldehyde were placed and heated to 30° C. Through the dropping funnel, 135 gr of sulfur monochloride was introduced into the reactor over a period of 60 minutes to induce reaction, at a temperture of 30° to 38° C. After completion of the reaction, the reaction mixture was subjected to an aftertreatment in the same manner as in Example 1. When the organic layer was analyzed, the yield was found to be 65%. The oil was found to contain the target product in purity of 67% and also contain 13% of by-produced trisulfide. The gas chromatography chart of the oil showed peaks suggestive of numerous decomposition products. When this oil was distilled, the target compound was obtained in a purity of only 85%.

CONTROL 2

The procedure of control 1 was repeated, except that the time spend for addition of sulfur monochloride was changed from 60 minutes to five hours. The yield was 50% and the purity was only 49% and more impurities were contained than in Control 1.

What is claimed is:

1. In a method for the production of a dithiodialdehyde represented by the formula II:

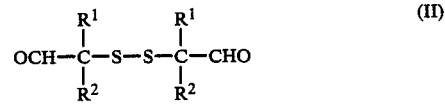

wherein $R^1$ and $R^2$ are independently alkyl group of 1 to 8 carbon atoms, by condensation of an active hydrogen-containing aldehyde represented by the formula I:

wherein $R^1$ and $R^2$ have the same meanings as defined above, with sulfur monochloride, the improvement which comprises simultaneously supplying said active hydrogen-containing aldehyde and sulfur monochloride to an inactive solvent.

2. A method according to claim 1, wherein the molar ratio of said active hydrogen-containing aldehyde to said sulfur monochloride in said inactive solvent is such that the amount of said sulfur monochloride falls in the range of 1.0 to 1.2 equivalent weights relative to the amount of said active hydrogen-containing aldehyde.

3. A method according to claim 2, wherein the reaction is carried out at a temperature in the range of 0° to 100° C.

4. A method according to claim 3, wherein $R^1$ and $R^2$ of said formula I independently stand for an alkyl group of 1 to 4 carbon atoms.

5. A method according to claim 3, wherein said active hydrogen-containing aldehyde is isobutyl aldehyde.

6. A method according to claim 3, wherein said inactive solvent is an aromatic hydrocarbon or a halogenated hydrocarbon.

7. In a method for the production of a dithiodialdehyde represented by the formual II:

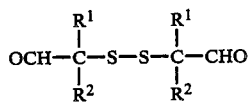    (II)

wherein $R^1$ and $R^2$ are independently alkyl group of 1 to 8 carbon atoms, by condensation of an active hydrogen-containing aldehydes represented by the formula I:

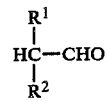    (I)

wherein $R^1$ and $R^2$ have the same meanings as defined above, with sulfur monochloride, the improvement which comprises adding said active hydrogen-containing aldehyde to a mixture of said inactive solvent with said sulfur monochloride thereby inducing reaction thereof with said sulfur monochloride in said mixture.

8. A method according to claim 7, wherein the molar ratio of said active hydrogen-containing aldehyde to said sulfur monochloride in said inactive solvent is such that the amount of said sulfur monochloride falls in the range of 1.0 to 1.2 equivalent weights relative to the amounts of said active hydrogen-containing aldehyde.

9. A method according to claim 8, wherein the reaction is carried out at a temperature in the range of 0° to 100° C.

10. A method according to claim 9, wherein $R^1$ and $R^2$ of said formula I independently stand for an alkyl group of 1 to 4 carbon atoms.

11. A method according to claim 9, wherein said active hydrogen-containing aldehyde is isobutyl aldehyde.

12. A method according to claim 9, wherein said inactive solvent is an aromatic hydrocarbon or a halogenated hydrocarbon.

* * * * *